United States Patent
Richard

(10) Patent No.: US 8,221,730 B2
(45) Date of Patent: Jul. 17, 2012

(54) SILANIC PARA-AMINOBENZALMALONATE-SUBSTITUTED S-TRIAZINE COMPOUNDS AND PHOTOPROTECTIVE COMPOSITIONS COMPRISED THEREOF

(75) Inventor: Hervé Richard, Villepinte (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/178,673

(22) Filed: Jul. 8, 2011

(65) Prior Publication Data

US 2011/0263846 A1    Oct. 27, 2011

Related U.S. Application Data

(62) Division of application No. 11/062,564, filed on Feb. 23, 2005.

(60) Provisional application No. 60/563,814, filed on Apr. 21, 2004.

(51) Int. Cl.
| | |
|---|---|
| A61K 8/00 | (2006.01) |
| A61K 8/18 | (2006.01) |
| A61Q 17/04 | (2006.01) |
| C07D 251/54 | (2006.01) |
| C07D 403/00 | (2006.01) |
| C07D 251/48 | (2006.01) |

(52) U.S. Cl. ........... 424/59; 544/197; 544/198; 544/206
(58) Field of Classification Search ...... 424/59; 544/197, 198, 206
See application file for complete search history.

(56) References Cited

U.S. PATENT DOCUMENTS

| | | | |
|---|---|---|---|
| 595,509 | A | 9/1999 | Granger et al. |
| 608,088 | A | 6/2000 | Richard et al. |
| 6,517,742 | B1 | 2/2003 | Richard et al. |
| 2002/0016488 | A1 | 2/2002 | Forestier et al. |

FOREIGN PATENT DOCUMENTS

| | | |
|---|---|---|
| EP | 0 841 341 A1 | 5/1998 |
| JP | H10-139648 | 9/1993 |
| JP | H-5-230040 | 5/1998 |
| JP | 2000-063388 | 2/2000 |

OTHER PUBLICATIONS

French Search Report corresponding to FR 04/50336 issued on Oct. 6, 2004.
English Translation of Notice of Rejection issued in Japanese Application No. 2005-048339 on Dec. 2, 2008.

Primary Examiner — Sreenni Padmanabhan
Assistant Examiner — Luke Karpinski
(74) Attorney, Agent, or Firm — Buchanan Ingersoll & Rooney PC

(57) ABSTRACT

UV-photoprotective sunscreen compositions contain at least one novel silanic p-aminobenzalmalonate-substituted s-triazine compound having the general formula (I):

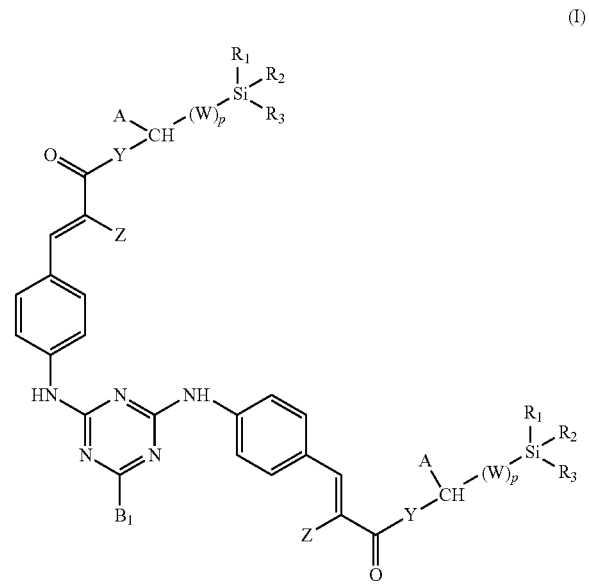

(I)

13 Claims, No Drawings

SILANIC PARA-AMINOBENZALMALONATE-SUBSTITUTED S-TRIAZINE COMPOUNDS AND PHOTOPROTECTIVE COMPOSITIONS COMPRISED THEREOF

CROSS-REFERENCE TO PARENT/PRIORITY APPLICATIONS

This application is a divisional, of U.S. patent application Ser. No. 11/062,564, filed Feb. 23, 2005, and also claims priority under 35 U.S.C. §119 of FR 04/50336, filed Feb. 24, 2004, and under 35 U.S.C. §120 of U.S. Provisional Application No. 60/563,814, filed Apr. 21, 2004, each hereby expressly incorporated by reference and each assigned to the assignee hereof.

BACKGROUND OF THE INVENTION

1. Technical Field of the Invention

The present invention relates to novel s-triazine compounds containing at least 2 specific para-aminobenzalmalonate substituents and to various cosmetic applications thereof.

The present invention also relates to photoprotective compositions comprising said s-triazine compounds comprising at least 2 grafted para-aminobenzalmalonate substituents as sunscreens active in the UV radiation region.

2. Description of Background and/or Related and/or Prior Art

It is known that radiation with wavelengths of from 280 nm to 400 nm makes possible browning of the human epidermis and that radiation with wavelengths of from 280 to 320 nm, known under the name of UV-B radiation, causes erythemas and skin burns which may be harmful to the development of natural tanning.

It is also known that UV-A rays, with wavelengths of from 320 to 400 nm, which cause browning of the skin, are capable of causing a detrimental change in the latter, in particular in the case of sensitive skin and/or of skin continually exposed to solar radiation. UV-A rays cause, in particular, a loss of elasticity of the skin and the appearance of wrinkles, resulting in premature cutaneous aging. They promote the triggering of the erythemal reaction or accentuate this reaction in certain individuals and can even be the cause of phototoxic or photoallergic reactions. Thus, for aesthetic and cosmetic reasons, such as the retention of the natural elasticity of the skin, individuals increasingly desire to control the effect of UV-A radiation on their skin. The term "sun protection factor" is understood to mean the ratio of the irradiation time necessary to reach the erythemogenic threshold in the presence of the screening agent tested to the irradiation time necessary to reach the same threshold in the absence of screening agent.

It is therefore desirable to have available compounds capable of absorbing UV-A rays.

In addition to their power in screening out UV-A radiation, the desired photoprotective compounds must also exhibit good cosmetic properties, good solubility in conventional solvents and in particular in fatty substances, such as oils and fats, and also good resistance to water and to sweat (persistence) and a satisfactory photostability.

Particularly exemplary such compounds which have been recommended for this purpose are the s-triazine derivatives bearing benzalmalonate substituents, described in EP-0,507,691 assigned to the assignee hereof. However, these compounds possess a liposolubility and photochemical stability which are not yet entirely satisfactory.

SUMMARY OF THE INVENTION

A novel family of s-triazine compounds bearing at least 2 silanic para-aminobenzalmalonate substituents has, surprisingly, now been developed having good absorbent properties in the long UV-A rays range and exhibiting a solubility in fatty substances, a photostability and cosmetic qualities which are markedly improved with respect to the s-triazine derivatives grafted by benzalmalonates of the prior art.

The present invention thus features a novel family of s-triazine compounds bearing at least 2 specific para-aminobenzalmalonate substituents and having the formula (I) as defined below.

This invention also features cosmetic or dermatological compositions suited for the photoprotection of keratinous substances/substrates, comprising, formulated into a cosmetically acceptable medium, at least one compound of formula (I) below.

DETAILED DESCRIPTION OF BEST MODE AND SPECIFIC/PREFERRED EMBODIMENTS OF THE INVENTION

More particularly, the compounds in accordance with the present invention have the following general formula (I):

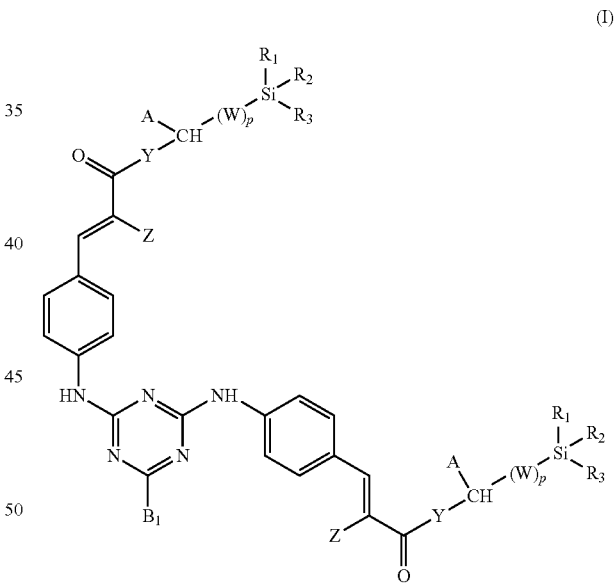

in which the radicals $R_1$, $R_2$ and $R_3$, which may be identical or different, are each a saturated or unsaturated and linear or branched $C_1$-$C_{10}$ alkyl radical optionally substituted with one or more halogen atoms (for example Cl, Br or F), or a phenyl radical; p is equal to 0 or 1; A is hydrogen, a saturated or unsaturated and linear or branched $C_1$-$C_8$ alkyl radical, a phenyl radical, the $Si(CH_3)_3$ group, with the proviso that, when A is $Si(CH_3)_3$, then p=0 and $R_1$, $R_2$ and $R_3$ are each methyl radicals; W is a saturated or unsaturated and linear or branched $C_1$-$C_8$ alkylene radical optionally substituted by a hydroxyl group; Z is —(C=O)OR$_4$, —(C=O)R$_5$, —(C=O)NR$_6$R$_7$, —SO$_2$R$_8$, —CN or —(C=O)YCHA $(W)_pSiR_1R_2R_3$; the $R_4$ radical is hydrogen, a saturated or unsaturated and linear or branched $C_1$-$C_{20}$ alkyl radical; the $R_5$ radical is a linear or branched, optionally cyclic, $C_1$-$C_{20}$ alkyl radical, or a $C_6$-$C_{12}$ aryl radical; the $R_6$ and $R_7$ radicals, which may be identical or different, are each hydrogen, or a linear or branched $C_1$-$C_{20}$ alkyl radical; Y is —O— or —$NR_7$—; the $R_8$ radical is a linear or branched $C_1$-$C_{20}$ alkyl radical, or a $C_6$-$C_{12}$ aryl radical; and $B_1$ is a chromophoric group selected from among the group consisting of para-aminobenzalmalonate, aminobenzimidazole, benzimidazole, aminobenzoate, aminosalicylate, anthranilate, aminobenzylidenecamphor, aminobenzotriazole, aminobenzoxazole or para-aminophenylbenzoxazole substituents, with the proviso that $B_1$ can also be a linear or branched $C_1$-$C_{20}$ aminoalkyl radical, or a $C_6$-$C_{20}$ aryl radical which can be unsubstituted or substituted by alkyl, hydroxyl and/or alkoxy radicals.

Although only the isomers in which the Z substituent is in the cis position with respect to the substituent with the aromatic ring are represented in the above formula (I), this formula should be understood as also encompassing the corresponding trans isomers.

In the above formula (I), the alkyl radicals can be saturated or unsaturated and linear or branched and are selected, in particular, from among the methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The alkyl radical which is particularly preferred is the methyl radical.

In the above formula (I), the alkoxy radicals are saturated or unsaturated and linear or branched and preferably selected from among the methoxy, ethoxy, n-propyloxy and n-butyloxy radicals.

In the above formula (I), the aryl radicals are preferably phenyl radicals.

According to a specific embodiment of the invention, the compounds of formula (I) can comprise 3 silanic para-aminobenzalmalonate groups, namely, that $B_1$ is a substituent of following formula (II):

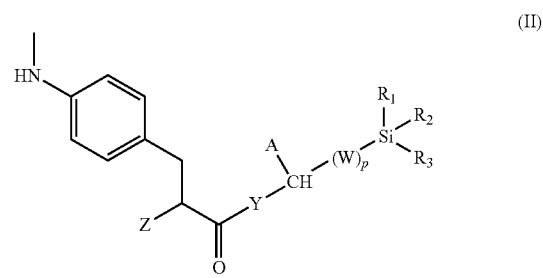

(II)

in which Z, A, p, W, $R_1$, $R_2$ and $R_3$ have the same definitions indicated above.

The compounds of formula (I) preferably exhibit at least one and more preferably still all of the following characteristics:
Z=—(C=O)$OR_5$, —CN or (C=O)YCHA$(W)_pSiR_2R_3R_4$,
$R_5$ is methyl or ethyl,
A is H,
$R_2$ to $R_4$ are each $C_1$-$C_4$ alkyl and more preferably methyl,
n is 0,
p is 0 or 1,
W is a $C_1$-$C_2$ alkylene radical.

Particularly preferred compounds of formula (I) are selected from among the compounds of the following formulae (1) to (6):

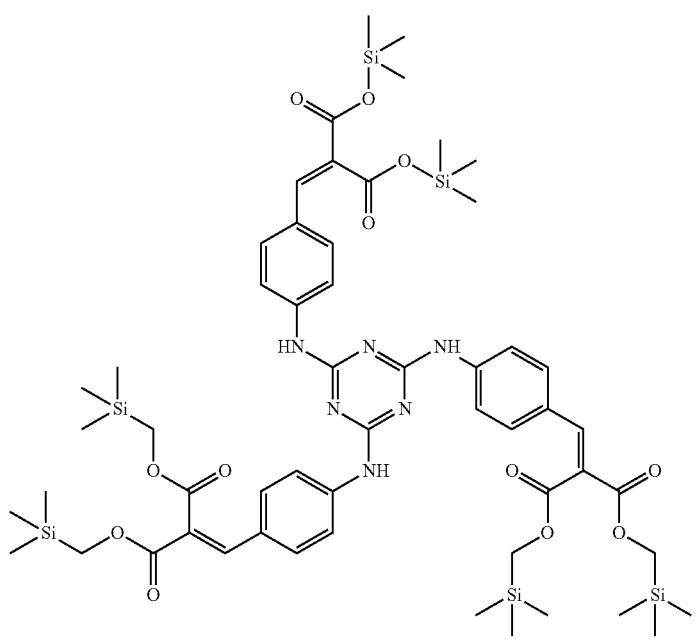

(1)

-continued
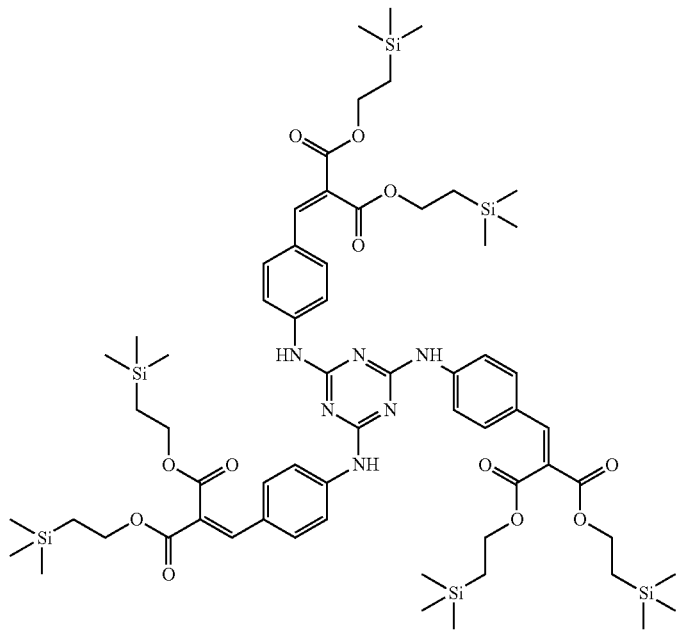
(2)
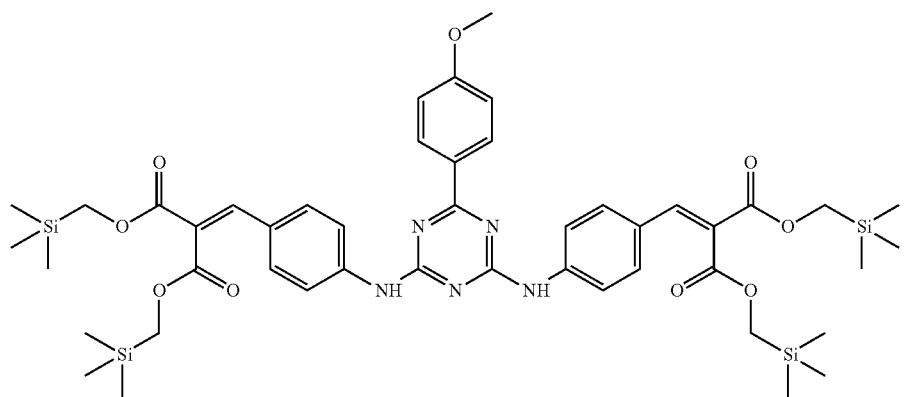
(3)
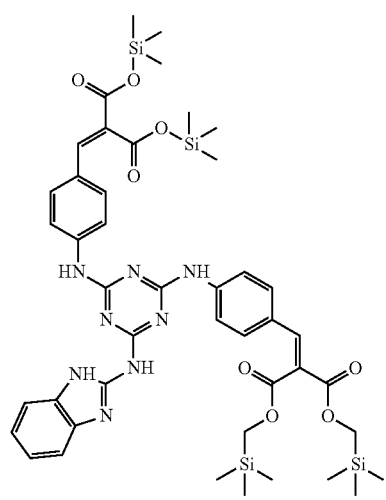
(4)
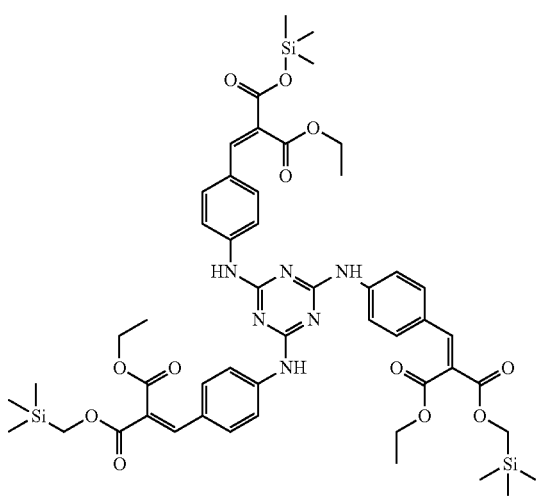
(5)

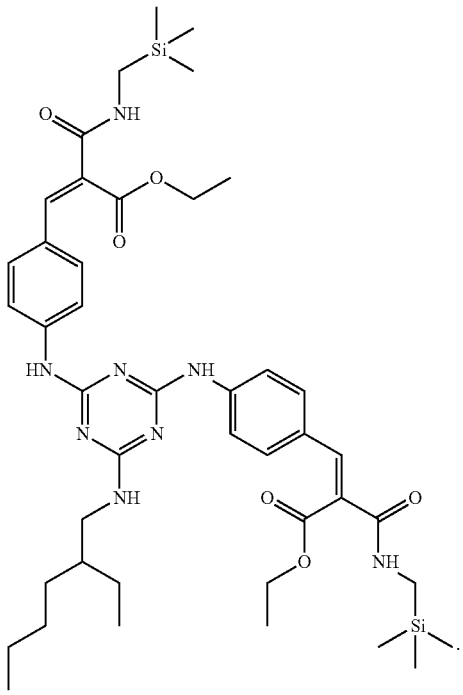

(6)

The compounds of formula (I) can be prepared according to the following scheme (a):

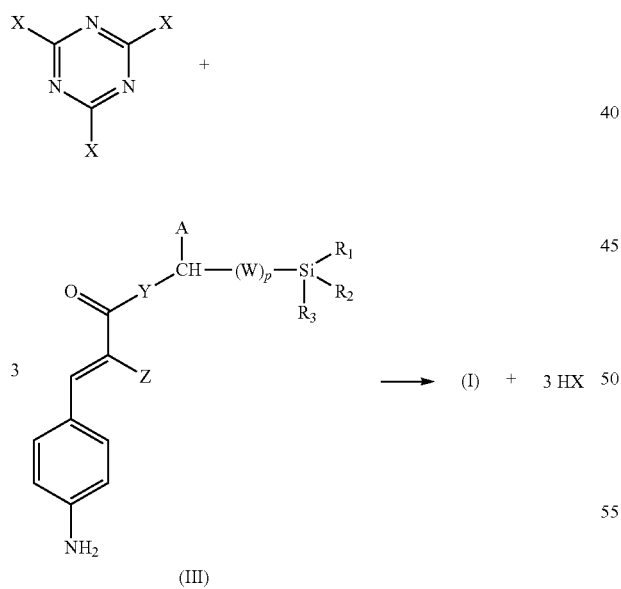

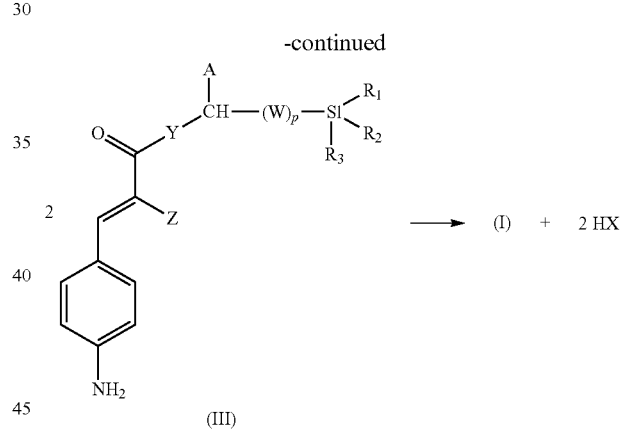

in which $R_1$, $R_2$, $R_3$, A, $B_1$, Y, W, Z and p have the definitions of the formula (I) above and X represents a halogen, in particular chlorine or bromine.

The above reactions can optionally be carried out in the presence of a solvent (for example: toluene, xylene or acetone/water), at a temperature of from 0° C. to 250° C., more particularly from 5° C. to 150° C.

The compounds of formula (III) can be prepared according to known methods described, for example, in EP-0,507,691 assigned to the assignee hereof.

In the case where Y is —O—, the compounds of the formula (I) can also be prepared by transesterification of derivatives of formula (IV) according to the following scheme (b):

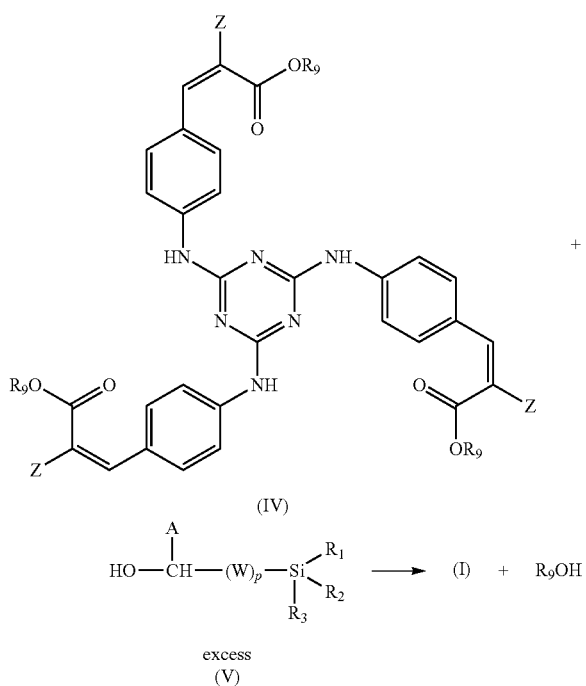

in which $R_1$, $R_2$, $R_3$, A, W, Z and p have the definitions of the formula (I) above and $R_9$ is methyl or ethyl.

The compounds of formula (I) are generally present in the compositions of the invention in proportions of from 0.01% to 20% by weight, preferably from 0.1% to 10% by weight, with respect to the total weight of the composition.

Furthermore, the compositions in accordance with the invention can comprise other additional organic or inorganic UV screening agents active in the UV-A and/or UV-B region which are water-soluble or fat-soluble or else insoluble in the cosmetic solvents commonly employed.

The additional organic screening agents are selected, in particular, from among anthranilates; cinnamic derivatives; dibenzoylmethane derivatives; salicylic derivatives; camphor derivatives; triazine derivatives other than those of the invention, such as those described in U.S. Pat. No. 4,367,390, EP-863,145, EP-517,104, EP-570,838, EP-796,851, EP-775, 698, EP-878,469, EP-933,376, EP-507,691, EP-507,692, EP-790,243 and EP-944,624; benzophenone derivatives; β,β-diphenylacrylate derivatives; benzotriazole derivatives; benzalmalonate derivatives; benzimidazole derivatives; imidazolines; bis-benzoazolyl derivatives, as described in EP-669,323 and U.S. Pat. No. 2,463,264; p-aminobenzoic acid (PABA) derivatives; methylenebis(hydroxyphenylbenzotriazole) derivatives, as described in U.S. Pat. Nos. 5,237, 071, 5,166,355, GB-2,303,549, DE-197,26,184 and EP-893, 119; benzoxazole derivatives, as described in EP-0,832,642, EP-1,027,883, EP-1,300,137 and DE-10162844; screening polymers and screening silicones, such as those described, in particular in WO 93/04665; dimers derived from α-alkylstyrene, such as those described in DE-19855649; 4,4-diarylbutadienes, as described in EP-0,967,200, DE-19746654, DE-19755649, EP-A-1,008,586, EP-1,133,980 and EP-133, 981; and mixtures thereof.

Exemplary additional organic screening agents are set forth below under their INCI names:

para-Aminobenzoic Acid Derivatives:
PABA,
Ethyl PABA,
Ethyl Dihydroxypropyl PABA,
Ethylhexyl Dimethyl PABA, sold in particular under the name "Escalol 507" by ISP,
Glyceryl PABA,
PEG-25 PABA, sold under the name "Uvinul P25" by BASF,
Salicylic Derivatives:
Homosalate, sold under the name "Eusolex HMS" by Rona/EM Industries, Ethylhexyl Salicylate, sold under the name "Neo Heliopan OS" by Haarmann and Reimer,
Dipropyleneglycol Salicylate, sold under the name "Dipsal" by Scher, TEA Salicylate, sold under the name "Neo Heliopan TS" by Haarmann and Reimer,
Dibenzoylmethane Derivatives:
Butyl Methoxydibenzoylmethane, sold in particular under the trademark "Parsol 1789" by Hoffmann-LaRoche,
Isopropyl Dibenzoylmethane,
Cinnamic Derivatives:
Ethylhexyl Methoxycinnamate, sold in particular under the trademark "Parsol MCX" by Hoffmann-LaRoche,
Isopropyl Methoxycinnamate,
Isoamyl Methoxycinnamate, sold under the trademark "Neo Heliopan E 1000" by Haarmann and Reimer,
Cinoxate, DEA Methoxycinnamate, Diisopropyl Methyl Cinnamate,
Glyceryl Ethylhexanoate Dimethoxycinnamate,
β,β-Diphenylacrylate Derivatives:
Octocrylene, sold in particular under the trademark "Uvinul N539" by BASF,
Etocrylene, sold in particular under the trademark "Uvinul N35" by BASF,
Benzophenone Derivatives:
Benzophenone-1, sold under the trademark "Uvinul 400" by BASF,
Benzophenone-2, sold under the trademark "Uvinul D50" by BASF,
Benzophenone-3 or Oxybenzone, sold under the trademark "Uvinul M40" by BASF,
Benzophenone-4, sold under the trademark "Uvinul MS40" by BASF,
Benzophenone-5,
Benzophenone-6, sold under the trademark "Helisorb 11" by Norquay,
Benzophenone-8, sold under the trademark "Spectra-Sorb UV-24" by American Cyanamid,
Benzophenone-9, sold under the trademark "Uvinul DS-49" by BASF,
Benzophenone-12,
n-Hexyl 2-(4-diethylamino-2-hydroxybenzoyl)benzoate,
Benzylidenecamphor Derivatives:
3-Benzylidene camphor, manufactured under the name "Mexoryl SD" by Chimex,
4-Methylbenzylidene camphor, sold under the name "Eusolex 6300" by Merck,
Benzylidene Camphor onic Acid, manufactured under the name "Mexoryl SL" by Chimex,
Camphor Benzalkonium Methoate, manufactured under the name "Mexoryl SO" by Chimex,
Terephthalylidene Dicamphor onic Acid, manufactured under the name "Mexoryl SX" by Chimex,
Polyacrylamidomethyl Benzylidene Camphor, manufactured under the name "Mexoryl SW" by Chimex, Phenylbenzimidazole Derivatives:
Phenylbenzimidazole onic Acid, sold in particular under the trademark "Eusolex 232" by Merck,
Disodium Phenyl Dibenzimidazole Tetraonate, sold under the trademark "Neo Heliopan AP" by Haarmann and Reimer,
Triazine Derivatives:
Anisotriazine, sold under the trademark "Tinosorb S" by Ciba-Geigy,
Ethylhexyl triazone, sold in particular under the trademark "Uvinul T150" by BASF,
Diethylhexyl Butamido Triazone, sold under the trademark "Uvasorb HEB" by Sigma 3V,
Phenylbenzotriazole Derivatives:
Drometrizole Trisiloxane, sold under the name "Silatrizole" by Rhodia Chimie,
Methylene Bis-Benzotriazolyl Tetramethylbutylphenol, sold in the solid form under the trademark "Mixxim BB/100" by Fairmount Chemical or in the micronized form in aqueous dispersion under the trademark "Tinosorb M" by Ciba Specialty Chemicals,
Anthranilic Derivatives:
Menthyl anthranilate, sold under the trademark "Neo Heliopan MA" by Haarmann and Reimer,
Imidazoline Derivatives:
Ethylhexyl Dimethoxybenzylidene Dioxoimidazoline Propionate,
Benzalmalonate Derivatives:
Polyorganosiloxanes with benzalmalonate functional groups, such as Polysilicone-15, sold under the trademark "Parsol SLX" by Hoffmann-LaRoche,
4,4-Diarylbutadiene Derivatives:
1,1-Dicarboxy(2,2'-dimethylpropyl)-4,4-diphenylbutadiene,
Benzoxazole Derivatives:
2,4-Bis[5-1(dimethylpropyl)benzoxazol-2-yl-(4-phenyl)-imino]-6-(2-ethylhexyl)imino-1,3,5-triazine, sold under the name Uvasorb K2A by Sigma 3V; and their mixtures.

The preferred additional organic UV screening agents are selected from among:
Ethylhexyl Salicylate,
Ethylhexyl Methoxycinnamate,
Butyl Methoxydibenzoylmethane,
Octocrylene,
Phenylbenzimidazole onic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor onic Acid,
Disodium Phenyl Dibenzimidazole Tetraonate,
Anisotriazine,
Ethylhexyl triazone,
Diethylhexyl Butamido Triazone,
Methylene Bis-benzotriazolyl Tetramethylbutylphenol,
Drometrizole Trisiloxane,
Polysilicone-15,
1,1-Dicarboxy(2,2'-dimethylpropyl)-4,4-diphenylbutadiene,
2,4-Bis[5-1(dimethylpropyl)benzoxazol-2-yl-(4-phenyl)-imino]-6-(2-ethylhexyl)imino-1,3,5-triazine,
and mixtures thereof.

The additional inorganic screening agents are selected from among pigments or alternatively nanopigments (mean size of the primary particles: generally from 5 nm to 100 nm, preferably from 10 nm to 50 nm) formed of coated or uncoated metal oxides, such as, for example, nanopigments formed of titanium oxide (amorphous or crystalline in the rutile and/or anatase form), iron oxide, zinc oxide, zirconium oxide or cerium oxide, which are all UV photoprotective agents well known per se. Conventional coating agents are furthermore alumina and/or aluminum stearate. Such nanopigments formed of coated or uncoated metal oxides are described, in particular, in EP-518,772 and EP-518,773.

The additional UV screening agents in accordance with the invention are generally present in the compositions according to the invention in proportions ranging from 0.01 to 20% by weight with respect to the total weight of the composition and preferably ranging from 0.1 to 10% by weight with respect to the total weight of the composition.

The cosmetic compositions according to the invention can additionally comprise agents for the artificial tanning and/or browning of the skin (self-tanning agents), such as dihydroxyacetone (DHA).

The compositions in accordance with the present invention can additionally comprise conventional cosmetic additives and adjuvants selected, in particular, from among fatty substances, organic solvents, ionic or nonionic thickeners, softening agents, humectants, antioxidants, moisturizing agents, desquamating agents, agents for combating free radicals, agents for combating pollution, anti-bacterials, anti-inflammatories, depigmenting agents, propigmenting agents, opacifiers, stabilizing agents, emollients, silicones, antifoaming agents, insect repellants, fragrances, preservatives, anionic, cationic, nonionic, zwitterionic or amphoteric surfactants, substance P antagonists, substance CGRP antagonists, fillers, pigments, polymers, propellants, basifying or acidifying agents, or any other ingredient commonly used in the cosmetics and/or dermatological field.

The fatty substances can be an oil or a wax or their mixtures. The term "oil" is understood to mean a compound which is liquid at ambient temperature. The term "wax" is understood to mean a compound which is solid or substantially solid at ambient temperature and which has a melting point generally of greater than 35° C.

Exemplary oils which can comprise the composition of the fatty phase are:
mineral oils, such as liquid paraffin and liquid petrolatum,
oils of animal origin, such as perhydrosqualene,
oils of vegetable origin, such as sweet almond oil, avocado oil, castor oil, olive oil, jojoba oil, sesame oil, groundnut oil, grape seed oil, rapeseed oil, coconut oil, hazelnut oil, karite butter, palm oil, apricot kernel oil, calophyllum oil, rice bran oil, maize germ oil, wheat germ oil, soybean oil, sunflower oil, evening primrose oil, safflower oil, passionflower oil and rye oil,
synthetic oils, such as purcellin oil, esters, such as, for example, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and esters derived from lanolic acid, such as isopropyl lanolate or isocetyl lanolate, isoparaffins and poly-α-olefins.

Mention may also be made, as other oils which can be formulated into the compositions according to the invention, of benzoates of $C_{12}$-$C_{15}$ fatty alcohols (Finsolv TN from Finetex), ethers, lipophilic derivatives of amino acids, such as isopropyl N-lauroylsarcosinate (Eldew SL-205 from Ajinomoto), fatty alcohols, such as lauryl alcohol, cetyl alcohol, myristyl alcohol, stearyl alcohol, palmityl alcohol, oleyl alcohol and 2-octyldodecanol, acetylglycerides, octanoates and decanoates of alcohols and of polyalcohols, such as those of glycol and of glycerol, ricinoleates of alcohols and of polyalcohols, such as those of cetyl, fatty acid triglycerides, such as caprylic/capric triglycerides or triglycerides of saturated $C_{10}$-$C_{18}$ fatty acids, fluorinated and perfluorinated oils, lanolin, hydrogenated lanolin, acetylated lanolin and, finally, volatile or non-volatile silicone oils.

Of course, the fatty phase can also comprise one or more conventional lipophilic cosmetic adjuvants, such as, for example, waxes, lipophilic gelling agents, surfactants or organic or inorganic particles, and in particular those which are already commonly used in the manufacture and the production of antisun/sunscreen cosmetic compositions.

Mention may be made, as waxy compounds, of paraffin wax, carnauba wax, beeswax or hydrogenated castor oil.

Mention may be made, among organic solvents, of lower alcohols and polyols. The latter can be selected from among glycols and glycol ethers, such as ethylene glycol, propylene glycol, butylene glycol, dipropylene glycol or diethylene glycol.

The thickeners can be selected, in particular, from among crosslinked acrylic polymers, such as the Carbomers, crosslinked acrylate/$C_{10}$-$C_{30}$ alkyl acrylate polymers of the Pemulen type or polyacrylate-3, sold under the name Viscophobe DB 1000 by Amerchol; polyacrylamides, such as the polyacrylamide, $C_{13}$-$C_{14}$ isoparaffin and laureth-7 emulsion sold under the name Sepigel 305 by Seppic, AMPS homopolymers or copolymers, such as Hostacerin AMPS sold by Clariant, modified or unmodified guar and cellulose gums, such as hydroxypropylated guar gum, methylhydroxyethylcellulose and hydroxypropylmethylcellulose, xanthan gum or nanometric silicas of Aerosil type.

Of course, one skilled in this art will take care to select the optional additional compound or compounds mentioned above and/or their amounts so that the advantageous properties intrinsically attached to the compounds in accordance with the invention are not, or not substantially, detrimentally affected by the envisaged addition or additions.

The compositions according to the invention can be prepared according to the techniques well known to this art, in particular those suited for the preparation of emulsions of oil-in-water or water-in-oil type.

The subject compositions can be provided, in particular, in the form of a simple or complex emulsion (O/W, W/O, O/W/O or W/O/W), such as a cream or a milk, or in the form of a gel or of a cream gel, in the form of a lotion, of an oil, of a powder or of a solid stick and can optionally be packaged as an aerosol and provided in the form of a foam or spray.

Preferably, the compositions according to the invention are provided in the form of an oil-in-water or water-in-oil emulsion.

When an emulsion, the aqueous phase thereof can comprise a nonionic vesicular dispersion prepared according to known processes (Bangham, Standish and Watkins, *J. Mol. Biol.*, 13, 238 (1965), FR-2,315,991 and FR-2,416,008).

When a cosmetic composition according to the invention is used for caring for the human epidermis, it can be provided in the form of a suspension or dispersion in solvents or fatty substances, in the form of a nonionic vesicular dispersion or in the form of an emulsion, preferably of oil-in-water type, such as a cream or a milk, or in the form of an ointment, gel, cream gel, suntan oil, solid stick, powder, aerosol foam or spray.

When a cosmetic composition according to the invention is used for caring for the hair, it can be provided in the form of a shampoo, lotion, gel, emulsion or nonionic vesicular dispersion and can constitute, for example, a rinse-out composition, to be applied before or after shampooing, before or after dyeing or bleaching, and before, during or after perming or hair straightening, a styling or treating lotion or a styling or treating gel, a lotion or a gel for blow drying or hair setting, or a composition for perming or straightening, dyeing or bleaching the hair.

When the composition is used as a product for making up the nails, lips, eyelashes, eyebrows or skin, such as a treatment cream for the epidermis, foundation, lipstick tube, eye shadow, face powder, mascara or eyeliner, it can be provided in the anhydrous or aqueous, pasty or solid form, such as oil-in-water or water-in-oil emulsions, nonionic vesicular dispersions, or suspensions.

By way of example, for the antisun formulations in accordance with the invention which exhibit a vehicle of oil-in-water emulsion type, the aqueous phase (comprising, in particular, the hydrophilic screening agents) generally represents from 50 to 95% by weight, preferably from 70 to 90% by weight, with respect to the entire formulation, the oily phase (comprising, in particular, the lipophilic screening agents) from 5 to 50% by weight, preferably from 10 to 30% by weight, with respect to the entire formulation, and the (co) emulsifier(s) from 0.5 to 20% by weight, preferably from 2 to 10% by weight, with respect to the entire formulation.

The compositions according to the invention can be provided in the form of vaporizable fluid lotions in accordance with the invention and can be applied to the skin or hair in the form of fine particles by means of pressurization devices. The devices in accordance with the invention are well known to one skilled in the art and comprise non-aerosol pumps or "atomizers", aerosol containers comprising a propellant, and aerosol pumps using compressed air as propellant. The latter are described in U.S. Pat. Nos. 4,077,441 and 4,850,517.

The compositions packaged as an aerosol in accordance with the invention generally comprise conventional propellants, such as, for example, hydrofluoro compounds, dichlorodifluoromethane, difluoroethane, dimethyl ether, isobutane, n-butane, propane or trichlorofluoromethane. They are preferably present in amounts ranging from 15 to 50% by weight with respect to the total weight of the composition.

This invention thus features formulating a compound of formula (I) as defined above into a cosmetic or dermatological composition as agent for screening out UV radiation.

The present invention also features formulating a compound of formula (I) as defined above into cosmetic compositions as agent for controlling the variation in the color of the skin due to UV radiation.

This invention also features the use of a compound of formula (I) as defined above as photostabilizing agent for synthetic polymers, such as plastics, or for glasses, in particular spectacle glasses or contact lenses.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Preparation of 2,4,6-tris(di(trimethylsilylmethyl) 4'-aminobenzalmalonate)-s-triazine

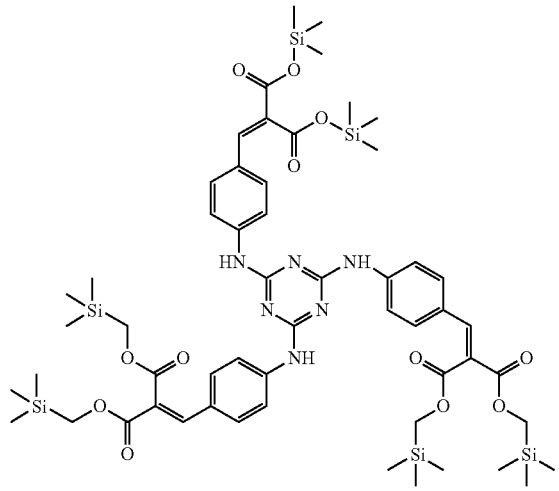

First Stage: Preparation of di(trimethylsilylmethyl) Malonate:

Malonic acid (8.3 g, 0.079 mol) and trimethylsilylmethyl alcohol (18.35 g, 0.176 mol) in 50 ml of toluene in the presence of 0.1 ml of concentrated sulphuric acid are refluxed for 3 hours in a reactor surmounted by a Dean and Stark apparatus. The water formed is removed by azeotropic distillation. The organic phase is washed 3 times with water and is dried over sodium sulphate. After filtering and evaporating the solvent under vacuum, 22 g of a colorless oil are obtained. After distillation under a vacuum of 0.15 mbar, the di(trimethylsilylmethyl) malonate fractions distilling at 74-76° C. are collected (19.6 g, Yield 90%) in the form of a colorless oil used as is in the following stage.

Second Stage: Preparation of di(trimethylsilylmethyl) 4-nitrobenzalmalonate:

p-Nitrobenzaldehyde (4.65 g, 0.03 mol) and di(trimethylsilylmethyl) malonate (8.5 g, 0.031 mol) are placed in 15 ml of toluene in a round-bottomed flask equipped with a Dean and Stark apparatus surmounted by a reflux condenser and sparged with nitrogen. The catalyst prepared in advance, acetic acid (0.2 ml) and piperidine (0.3 ml) in suspension in 0.5 ml of toluene, is added thereto. The mixture is refluxed for 5 hours with stirring and the water formed is removed via the Dean and Stark apparatus. Two further additions of the same amount of catalyst were necessary. The toluene is removed under vacuum and the residue is taken up in isopropyl ether and then washed twice with water. After drying the organic phase and evaporating the solvent, a red-brown oil is obtained. After purifying on a silica column (eluent: heptane/AcOEt 9/1), 7.1 g (Yield 57%) of clean di(trimethylsilylmethyl) 4-nitrobenzalmalonate fractions are collected in the form of a pale yellow solid used as is in the following stage.

Third Stage: Preparation of di(trimethylsilylmethyl) 4-aminobenzalmalonate:

The derivative from the preceding stage (3.2 g, 0.0078 mol) is dispersed in 5.5 ml of acetic acid with stirring and while sparging with nitrogen. 8 ml of water are added thereto. The mixture is heated to 50° C. Iron (4.36 g) is added thereto portionwise without exceeding a temperature of 55° C. (introduction time 1 hour). Subsequently, acetic acid (8 ml) is added dropwise without exceeding a temperature of 55° C. (introduction time 1 hour). Heating is carried out for an additional 45 minutes at 55° C. The mixture is cooled, dichloromethane is added and the mixture is filtered through celite. The organic phase is washed with water, with a saturated sodium bicarbonate solution and with water and is then dried over sodium sulphate. After concentrating under reduced pressure, an orange-colored oil is obtained and is purified by chromatography on a silica column (eluent: heptane/AcOEt 9/1). 1.8 g (Yield 62%) of clean di(trimethylsilylmethyl) 4-aminobenzalmalonate fractions are collected in the form of a yellow solid used as is in the following stage.

Fourth Stage: Preparation of the Derivative of Example 1:

The preceding derivative (1.1 g, 9.66×10$^{-4}$ mol), dissolved in 5 ml of toluene, is introduced dropwise at 0-5° C. into a dispersion of cyanuric chloride (0.18 g, 3.22×10$^{-4}$ mol) in 10 ml of toluene while sparging with nitrogen. The mixture is subsequently heated at reflux for 5 hours while degassing with nitrogen. After cooling, the organic phase is washed with water and then with an aqueous sodium bicarbonate solution. The organic phase is concentrated under reduced pressure. The residue obtained is dissolved in 1,2-dichloroethane. The organic phase is washed with water, with a saturated sodium bicarbonate solution and with water and is then dried over sodium sulphate. After concentrating under reduced pressure, a yellow oil is obtained and is purified by chromatography on a silica column (eluent: heptane/AcOEt 85/15). 0.75 g (Yield 64%) of clean fractions of the derivative of Example 1 is collected in the form of a pale yellow gum:
UV (ethanol) $\lambda_{max}$=355 nm; $\epsilon_{max}$=118 970; $E_{1\%}$=987.

EXAMPLE 2

Preparation of 2,4,6-tris(di(trimethylsilylethyl) 4'-aminobenzalmalonate)-s-triazine

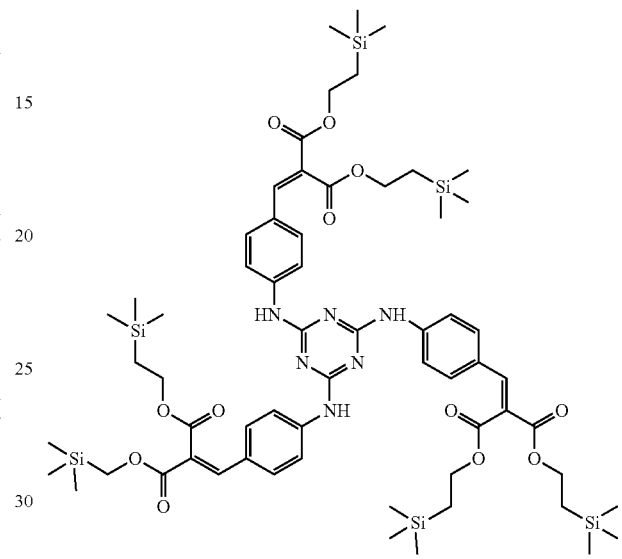

2,4,6-Tris(diethyl 4'-aminobenzalmalonate)-s-triazine (1 g, 1.16×10$^{-4}$ mol) (Example 1 of Application EP 0,507,691) is dissolved in 5 ml of trimethylsilylethyl alcohol while sparging with nitrogen. The mixture is subsequently heated at reflux for 25 hours with 0.2 g of para-toluenesulphonic acid. After addition of 30 ml of dichloromethane, the organic phase is washed with water and then with an aqueous sodium bicarbonate solution, and dried. It is concentrated under reduced pressure. The residue obtained is purified by chromatography on a silica column (eluent: heptane/AcOEt 85/15). 0.35 g (Yield 32%) of the derivative of Example 2 is collected in the form of a pale yellow gum:
UV (ethanol) $\lambda_{max}$=355 nm; $\epsilon_{max}$=125 250; $E_{1\%}$=965.

EXAMPLE 3

Preparation of 2,4-bis(di(trimethylsilylmethyl) 4'-aminobenzalmalonate)-6-(para-methoxyphenyl)-s-triazine

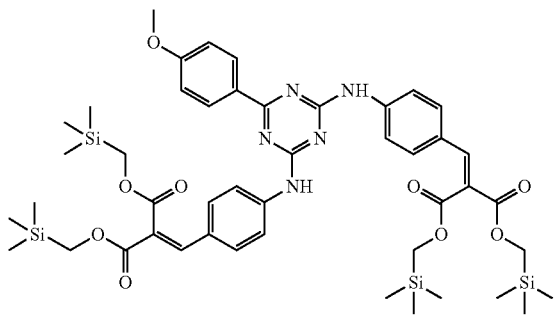

2,4-Dichloro-6-(para-methoxyphenyl)-s-triazine (0.67 g, 2.61×10$^{-3}$ mol) is dispersed in 10 ml of toluene. A solution in 10 ml of di(trimethylsilylmethyl) 4-aminobenzalmalonate (2 g, 5.2×10$^{-3}$ mol) is added thereto dropwise while sparging with nitrogen. The mixture is refluxed for 4 hours, 30 minutes. After an addition of 20 ml of dichloromethane, the organic phase is washed with water, with a saturated sodium bicarbonate solution and with water and is then dried over sodium sulphate. The organic phase is concentrated under vacuum. The residue is subjected to separation on a silica column (eluent: heptane/EtOAc 8/2). Clean fractions are recovered in the form of a pale yellow oil which is precipitated from an ethanol/heptane mixture to produce the derivative of Example 3 (1.42 g, Yield 58%) in the form of an amorphous pale yellow powder:
UV (ethanol) $\lambda_{max}$=351 nm; $\epsilon_{max}$=74 540; $E_{1\%}$=791,
$\lambda_{max}$=340 nm; $\epsilon_{max}$=74 450; $E_{1\%}$=790,
$\lambda_{max}$=296 nm; $\epsilon_{max}$=28 280; $E_{1\%}$=340.

EXAMPLE 4

Preparation of 2,4-bis(di(trimethylsilylmethyl) 4'-aminobenzalmalonate)-6-(2'-aminobenzimidazole)-s-triazine

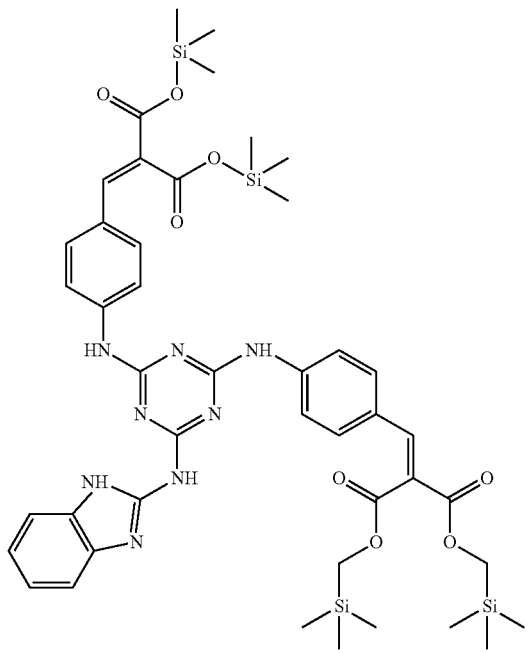

First stage: Preparation of 2,4-dichloro-6-(2'-aminobenzimidazole)-s-triazine:

Cyanuric chloride (18 g, 0.097 mol) is dissolved at 0° C. in 150 ml of acetone. 50 ml of water are added thereto. A suspension of 2-aminobenzimidazole (13 g, 0.097 mol) in 100 ml of acetone is added thereto dropwise at 0° C. while sparging with nitrogen. A solution of sodium carbonate (7 g) in 150 ml of water is added thereto. The heterogeneous mixture is left stirring at 0-5° C. for 2 hours. The reaction mixture is filtered. The solid is washed with dichloromethane, with water and with a small amount of acetone. After drying, 25 g (Yield 91%) of 2,4-dichloro-6-(2'-aminobenzimidazole)-s-triazine are recovered in the form of a beige powder used as is in the following stage.

Second Stage: Preparation of the Derivative of Example 4:

The preceding derivative (0.267 g, 9.5×10$^{-4}$ mol) is dispersed with di(trimethylsilylmethyl) 4-aminobenzalmalonate (0.72 g, 1.9×10$^{-3}$ mol) in 10 ml of toluene. The mixture is refluxed for 4 hours, 30 minutes. The organic phase is concentrated under vacuum. After an addition of 20 ml of dichloromethane, the organic phase is washed with water, with a saturated sodium bicarbonate solution and with water and is then dried over sodium sulphate. After crystallization from a dichloromethane/MeOH mixture, the derivative of Example 4 is obtained (0.66 g, Yield 72%) in the form of an amorphous light brown powder:
UV (ethanol)
$\lambda_{max}$=342 nm; shoulder $\epsilon_{max}$=61 910; $E_{1\%}$=640,
$\lambda_{max}$=325 nm; $\epsilon_{max}$=76 420; $E_{1\%}$=790.

Example of Formulation in an O/W Emulsion:

| CHEMICAL NAME<br>COMMERCIAL REFERENCE - SUPPLIER | COMPOSITION (g %) |
|---|---|
| GLYCERYL MONOSTEARATE/POLYETHYLENE GLYCOL STEARATE (100 EO) MIXTURE<br>SIMULSOL 165 - Seppic | 1 |
| STEARIC ACID<br>STEARINE TP 1200 PASTILLES - Stéarinerie Dubois | 1.5 |
| POLYDIMETHYLSILOXANE<br>200 FLUID 350 CS - Dow Corning | 0.5 |
| CETYL ALCOHOL<br>LANETTE 16 NF - Cognis | 0.5 |
| CETYLSTEARYL GLYCOSIDE/CETYLSTEARYL ALCOHOL MIXTURE<br>MONTANOV 68 - Seppic | 2 |
| PRESERVATIVE | 1 |
| TRIETHANOLAMINE<br>TRIETHANOLAMINE - BASF | 0.45 |
| CAPRIC/CAPRYLIC ACID TRIGLYCERIDE<br>MYRITOL 317 - Cognis | 10 |
| COMPOUND OF EXAMPLE 1 | 5 |
| GLYCEROL<br>PRICERINE 9091 - Uniquema | 5 |
| XANTHAN GUM<br>KELTROL T - CP Kelco | 0.1 |
| CROSSLINKED ACRYLIC ACID/$C_{10}$-$C_{30}$ ALKYL ACRYLATE COPOLYMER<br>PEMULEN TR-1 - Noveon | 0.12 |
| TRIETHANOLAMINE<br>TRIETHANOLAMINE - BASF | q.s. pH |
| DEMINERALIZED WATER | q.s. for 100 g |

Photostabilities Compared between a Compound of the Prior Art and the Compound According to the Invention of Example 1:

Products tested:

2,4,6-Tris(diisobutyl 4'-aminobenzalmalonate)-s-triazine=prior art (Example 1 of Patent EP 0,507,691).

2,4,6-Tris(di(trimethylsilylmethyl) 4'-aminobenzalmalonate)-s-triazine=Example 1 according to the invention.

The two products were dissolved at 5% by weight in the oil Miglyol 812. Approximately 10 mg of oily solution are spread over 10 cm$^2$ at the surface of a hollow disc of frosted glass; the amount is determined by weighing.

The films of the oily solutions are irradiated for one hour using an Oriel solar simulator (UV-A=14.2 mW/cm$^2$; UV-B=0.41 mW/cm$^2$), then extracted with 10 ml of ethanol comprising 10% of isopropanol and subjected to ultrasound for 5 min. The products are quantified by HPLC of the extracts.

HPLC conditions: column: UP5WOD-25QS, 250×4.6 mm, 5 μm, Interchrom; eluent: methanol (Comparative Example 1) and 96% of methanol+4% of water (Example 1); flow rate: 1 ml/min; volume injected: 10 μl; detection: diode array; rt (min): 5.2 (Comparative Example 1) and 13.8 (Example 1).

The degrees of loss are determined by comparison of the amounts of product present in the irradiated samples and in the non-irradiated controls prepared simultaneously and treated in the same way (means over 3 samples; S=surface/mg solution): % loss=$100 \times (S_0 - S_{irr})/S_0$ Photostability Results:

| Compound | Test | % of disappearance |
|---|---|---|
| Compound (prior art) | 1 | 11 |
| Compound (prior art) | 2 | 10 |
| Compound (prior art) | 3 | 9 |
| Example 1 | 4 | 0 |
| Example 1 | 5 | 0 |
| Example 1 | 6 | 0 |

Compound of the prior art: The loss in Miglyol is from 9 to 11% after exposure for one hour to the simulator of a 1 mg/cm² film of 5% solution.

Example 1: No loss in Miglyol is observed after exposure for one hour to the simulator of a 1 mg/cm² film of 5% solution.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A polysubstituted s-triazine compound having the following formula (I):

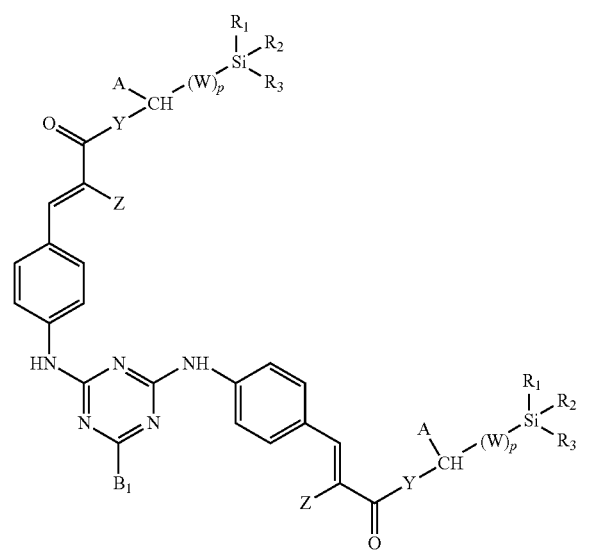

(I)

in which the radicals $R_1$, $R_2$ and $R_3$, which may be identical or different, are each a saturated or unsaturated and linear or branched $C_1$-$C_{10}$ alkyl radical optionally substituted with one or more halogen atoms, or a phenyl radical; p is equal to 0 or 1; A is hydrogen, a saturated or unsaturated and linear or branched $C_1$-$C_8$ alkyl radical, a phenyl radical, a Si(CH$_3$)$_3$ group, with the proviso that, when A is Si(CH$_3$)$_3$, then p=0 and $R_1$, $R_2$ and $R_3$ are each methyl radicals; W is a saturated or unsaturated and linear or branched $C_1$-$C_8$ alkylene radical optionally substituted by a hydroxyl group; Z is —(C=O)OR$_4$, —(C=O)R$_5$, —(C=O)NR$_6$R$_7$, —SO$_2$R$_8$, —CN or —(C=O)YCHA(W)$_p$SiR$_1$R$_2$R$_3$; the $R_4$ radical is hydrogen, a saturated or unsaturated and linear or branched $C_1$-$C_{20}$ alkyl radical; the $R_5$ radical is a linear or branched, optionally cyclic, $C_1$-$C_{20}$ alkyl radical, or a $C_6$-$C_{12}$ aryl radical; the $R_6$ and $R_7$ radicals, which may be identical or different, are each hydrogen, or a linear or branched $C_1$-$C_{20}$ alkyl radical; Y is —O— or —NR$_7$—; the $R_8$ radical is a linear or branched $C_1$-$C_{20}$ alkyl radical, or a $C_6$-$C_{12}$ aryl radical; and $B_1$ is a chromophoric group selected from among the group consisting of para-aminobenzalmalonate, aminobenzimidazole, benzimidazole, aminobenzoate, aminosalicylate, anthranilate, aminobenzylidenecamphor, aminobenzotriazole, aminobenzoxazole, para-aminophenylbenzoxazole substituents, a linear or branched $C_1$-$C_{20}$ aminoalkyl radical, or a $C_6$-$C_{20}$ aryl radical which can be unsubstituted or substituted by alkyl, hydroxyl and/or alkoxy radicals.

2. The polysubstituted s-triazine compound as defined by claim 1, wherein formula (I), Z is —(C=O)OR$_4$.

3. The polysubstituted s-triazine compound as defined by claim 1, wherein formula (I), Z is —(C=O)R$_5$.

4. The polysubstituted s-triazine compound as defined by claim 1, wherein formula (I), Z is —(C=O)NR$_6$R$_7$.

5. The polysubstituted s-triazine compound as defined by claim 1, wherein formula (I), Z is —SO$_2$R$_8$.

6. The polysubstituted s-triazine compound as defined by claim 1, wherein formula (I), Z is —CN.

7. The polysubstituted s-triazine compound as defined by claim 1, wherein formula (I), Z is —(C=O)YCHA(W)$_p$SiR$_1$R$_2$R$_3$.

8. The polysubstituted s-triazine compound as defined by claim 1, wherein formula (I), A is —Si(CH3)$_3$.

9. The polysubstituted s-triazine compound as defined by claim 1, wherein formula (I), Y is —O—.

10. The polysubstituted s-triazine compound as defined by claim 1, wherein formula (I), Y is —NR$_7$—.

11. The polysubstituted s-triazine compound as defined by claim 1, wherein formula (I), B$_1$ is a substituent having the following formula (II) wherein Z, Y, A, W, p, $R_1$, $R_2$, and $R_3$ are defined as in claim 1:

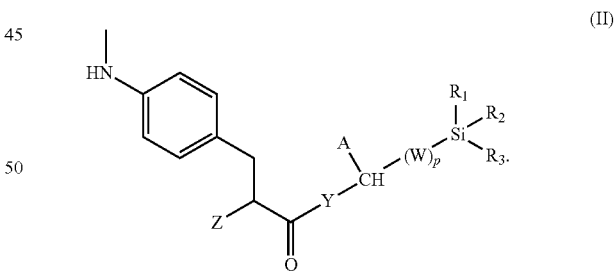

(II)

12. The polysubstituted s-triazine compound as defined by claim 1, wherein formula (I):
Z=—(C=O)OR$_5$, —CN or (C=O)YCHA(W)$_p$SiR$_2$R$_3$R$_4$,
R$_5$ is methyl or ethyl,
A is H,
$R_2$ to $R_4$ are each $C_1$-$C_4$ alkyl,
p is 0 or 1, and
W is a $C_1$-$C_2$ alkylene radical.

13. The polysubstituted s-triazine compound as defined by claim 1, selected from the group consisting of the following compounds (1) to (6):

(1)
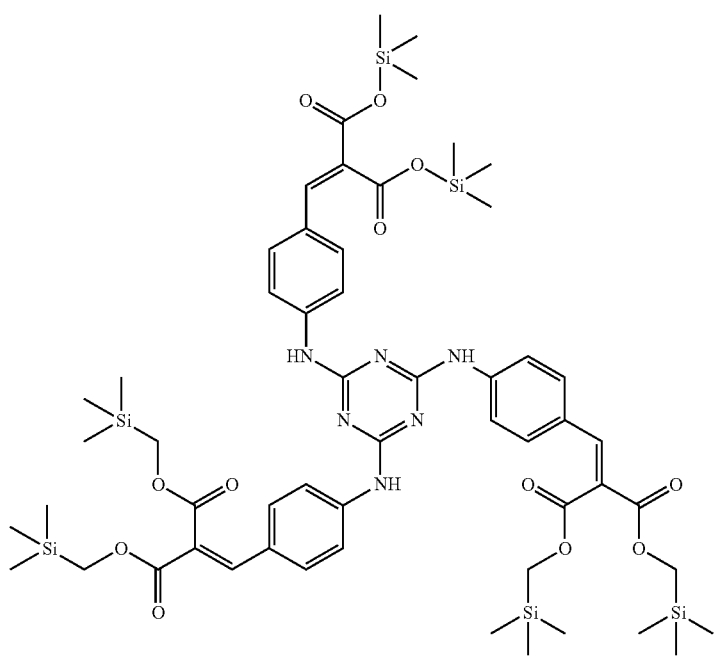
(2)
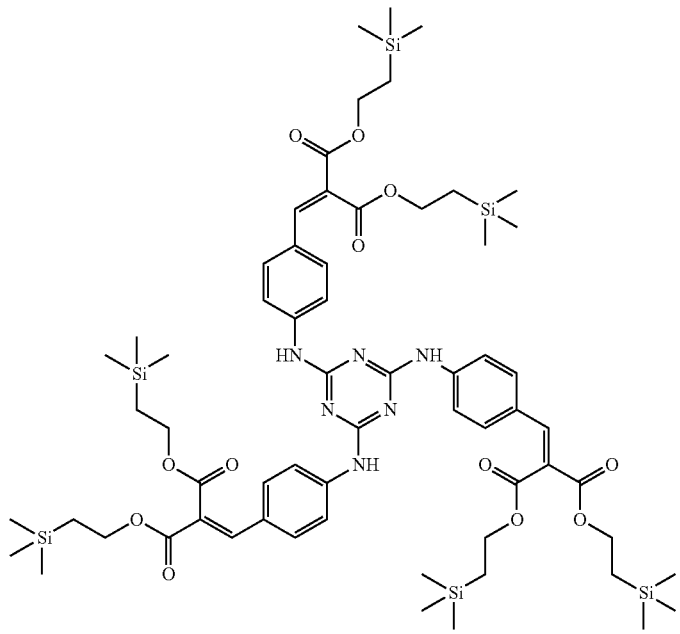
(3)
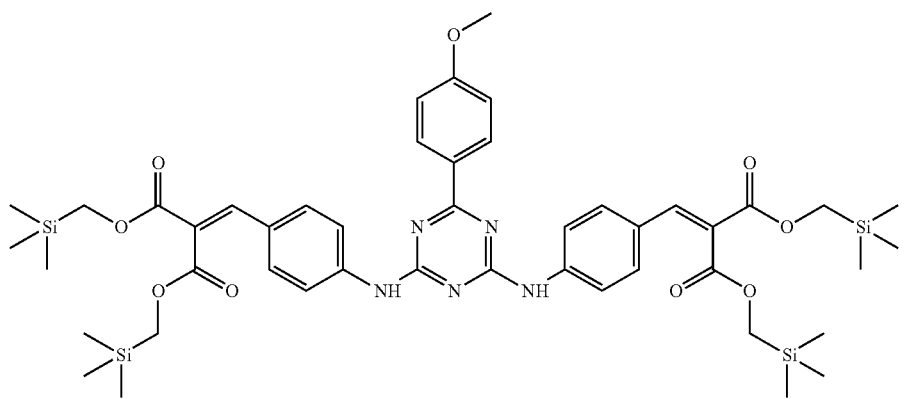

(4)
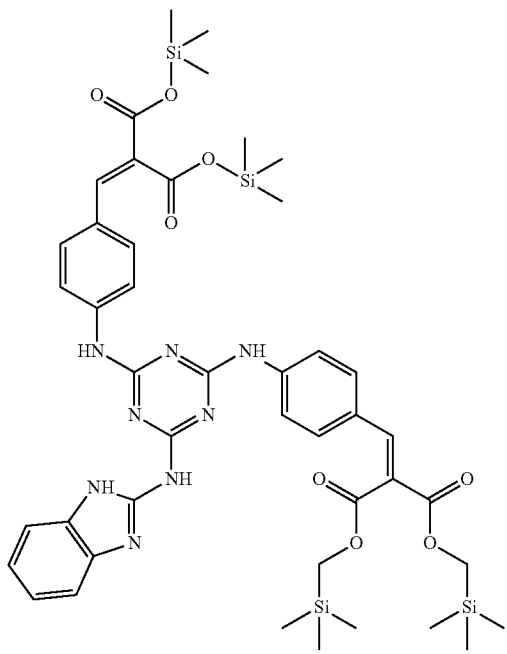
(5)
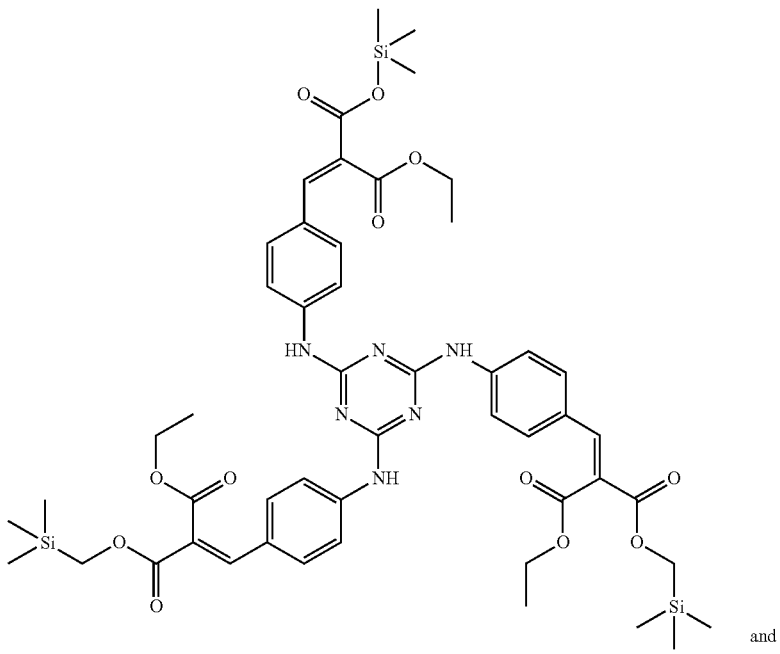
and

-continued
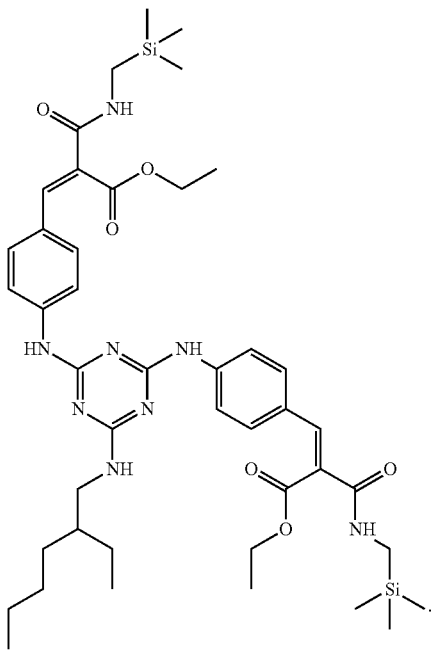
(6)

UNITED STATES PATENT AND TRADEMARK OFFICE
CERTIFICATE OF CORRECTION

PATENT NO. : 8,221,730 B2
APPLICATION NO. : 13/178673
DATED : July 17, 2012
INVENTOR(S) : Herve Richard Page 1 of 1

It is certified that error appears in the above-identified patent and that said Letters Patent is hereby corrected as shown below:

On the cover page, first column, Foreign Application Priority Data should read:

(30) Foreign Application Priority Data

February 24, 2004 (FR)    04/50336

Signed and Sealed this
Sixth Day of November, 2012

David J. Kappos
*Director of the United States Patent and Trademark Office*